United States Patent [19]
Jorgenson et al.

[11] Patent Number: 5,496,460
[45] Date of Patent: Mar. 5, 1996

[54] TWO DIMENSIONAL SEPARATION SYSTEM

[75] Inventors: James W. Jorgenson, Chapel Hill; Anthony V. Lemmo, Durham, both of N.C.

[73] Assignee: The University of North Carolina at Chapel Hill, Chapel Hill, N.C.

[21] Appl. No.: 359,614

[22] Filed: Dec. 20, 1994

Related U.S. Application Data

[63] Continuation of Ser. No. 28,678, Mar. 9, 1993, Pat. No. 5,389,221.

[51] Int. Cl.$^6$ .................... G01N 27/26; G01N 27/447
[52] U.S. Cl. ............................................ 204/604
[58] Field of Search ................ 204/299 R, 180.1; 137/842

[56] References Cited

U.S. PATENT DOCUMENTS

| | | | |
|---|---|---|---|
| 4,676,897 | 6/1987 | Kuze et al. | 210/198.2 |
| 4,708,782 | 11/1987 | Andresen et al. | 204/299 R |
| 5,131,998 | 7/1992 | Jorgenson et al. | 204/299 R |

OTHER PUBLICATIONS

Stephen L. Pentoney, Jr. et al, "On–Line Connector for Microcolumns: Application to the On–Column o–Phthaldialdehyde Derivation of Amino Acids Separated by Capillary Zone Electrophoresis", Analytical Chemistry, vol. 60, No. 23 (Dec. 1, 1988) 2625–2629.
P. Janssen et al., *Complementary information from isotachophoresis and high–performance liquid chromatography in peptide analysis*, Journal of Chromatography 470, 171–183 (1989).
R. G. Nielsen et al., *Capillary zone electrophoresis of peptide fragments from trypsin digestion of biosynthetic human growth hormone*, Journal of Chromatography 480, 393–401 (1989).
H. Yamamoto et al., *Gel Permeation Chromatography Combined with Capillary Electrophoresis for Microanalysis of Proteins*, Journal of Chromatography 480, 277–283 (1989).
S. L. Pentoney et al., *On–Line Connector for Microcolumns: Application to the On–Column o–Phthaldialdehyde Derivatization of Amino Acids Separated by Capillary Zone Electrophoresis*, Analytical Chemistry 60, No. 23, 2625–2629 (1988).

*Primary Examiner*—John Niebling
*Assistant Examiner*—John S. Starsiak, Jr.
*Attorney, Agent, or Firm*—Bell, Seltzer, Park & Gibson

[57] ABSTRACT

A combination liquid chromatography and capillary electrophoresis separation system is disclosed. The system comprises a flow gating interface having an effluent channel and a gating channel formed therein. The gating channel transversely intersects the effluent channel at an intersection portion so that the channels are in fluid communication with one another. The intersection portion divides the effluent channel into an upstream portion and a downstream portion, and divides the gating channel into an upstream portion and a downstream portion. A liquid chromatography column is connected to the effluent channel upstream portion and an electrophoresis capillary is connected to the effluent channel downstream portion. A flush solution inlet line is connected to said gating channel upstream portion, and a flush solution outlet line is connected to the gating channel downstream portion. A valve regulates the flow of flush solution from the flush solution inlet line to the gating channel upstream portion. The intersection portion is configured so that the rate of flow of effluent from the effluent channel upstream portion to the effluent channel downstream portion decreases as the rate of flow of flush solution in the gating channel increases.

22 Claims, 6 Drawing Sheets

TWO DIMENSIONAL SEPARATION SYSTEM

This invention was made with government support under Grant No. CHE-8912926 from the National Science Foundation. The government has certain rights to this invention.

This application is a continuation of prior application Ser. No. 08/028,678, filed Mar. 9, 1993, now U.S. Pat. No. 5,389,221 the disclosure of which is incorporated by reference herein in its entirety.

FIELD OF THE INVENTION

This invention relates to a two dimensional separation apparatus involving liquid chromatography followed by capillary electrophoresis.

BACKGROUND OF THE INVENTION

The analysis of complex mixtures often requires more than one separation process in order to resolve all the components present in a sample. It is for this reason that two dimensional (2D) separation schemes have been devised. When constructing a successful 2D system several criteria need to be addressed. Firstly, the two techniques should base their respective separations on as different a means as possible. Doing so will reduce the amount of redundant information contained in the 2D dataset. Secondly, the second dimension needs to operate at a sufficient rate of speed so that frequent "sampling" of the first dimension is achieved. This is necessary to ensure that the peak profiles obtained from the first separation dimension are not degraded. See Giddings, *Analytical Chem.* 56, 1258A (1984). Bushey and Jorgenson realized that capillary zone electrophoresis (CZE) is well suited as a second dimension separation due to the ability to obtain highly efficient separations with short run times. In 1990 they introduced the first fully automated 2D system, which coupled column liquid chromatography with CZE. See U.S. Pat. No. 5,131,998 (the disclosure of which is to be incorporated by reference), and Bushey and Jorgenson, *Analytical Chem.* 62, 978 (1990). In this system all sample components separated in the liquid chromatography dimension were subjected to separation by CZE (although the entire liquid chromatography elution volume was not reinjected for CZE). The coupling of the two dimensions was accomplished using conventional column and sample loop (valve loop system) technology.

A 2D system that coupled microcolumn liquid chromatography with CZE would be microscale, able to perform complete analyses with only a few hundred nanoliters of sample. Microcolumns (columns with an inner diameter $\leq 250$ μm) have been shown to be considerably more efficient than conventional size columns. The relative merits of using microcolumns rather than conventional columns has been previously discussed. See Kennedy and Jorgenson, *J. Microcolumn Separations* 2,120 (1990). However, microcolumns and their inherently small column volumes and operating flow rates pose an engineering problem in terms of designing a suitable interface for use with CZE, and it has not heretofore been suggested how microcolumn liquid chromatography might be coupled to CZE to provide a 2D chromatography system.

SUMMARY OF THE INVENTION

Disclosed herein is a method and apparatus that can be used, among other things, to couple microcolumn liquid chromatography with a capillary electrophoresis for the separation of various materials. Coupling of the systems is achieved using a novel interface termed "transverse flow gating".

In view of the foregoing, a first aspect of the present invention is a flow gating interface for use in coupling a liquid chromatography column to a capillary electrophoresis capillary. The flow gating interface has an effluent channel and a gating channel formed therein, the effluent channel for receiving effluent from a liquid chromatography column and the gating channel for receiving flush solution, with the gating channel transversely intersecting the effluent channel at an intersection portion so that the channels are in fluid communication with one another. The intersection portion divides the effluent channel into an upstream portion and a downstream portion, and the intersection portion divides the gating channel into an upstream portion and a downstream portion. The intersection portion is configured so that the rate of flow of effluent from the effluent channel upstream portion to the effluent channel downstream portion decreases as the rate of flow of flush solution in the gating channel increases.

The foregoing and other objects and aspects of the present invention are explained in detail in the drawings herein and the specification set forth hereinbelow.

DETAILED DESCRIPTION OF THE INVENTION

Figure 1:
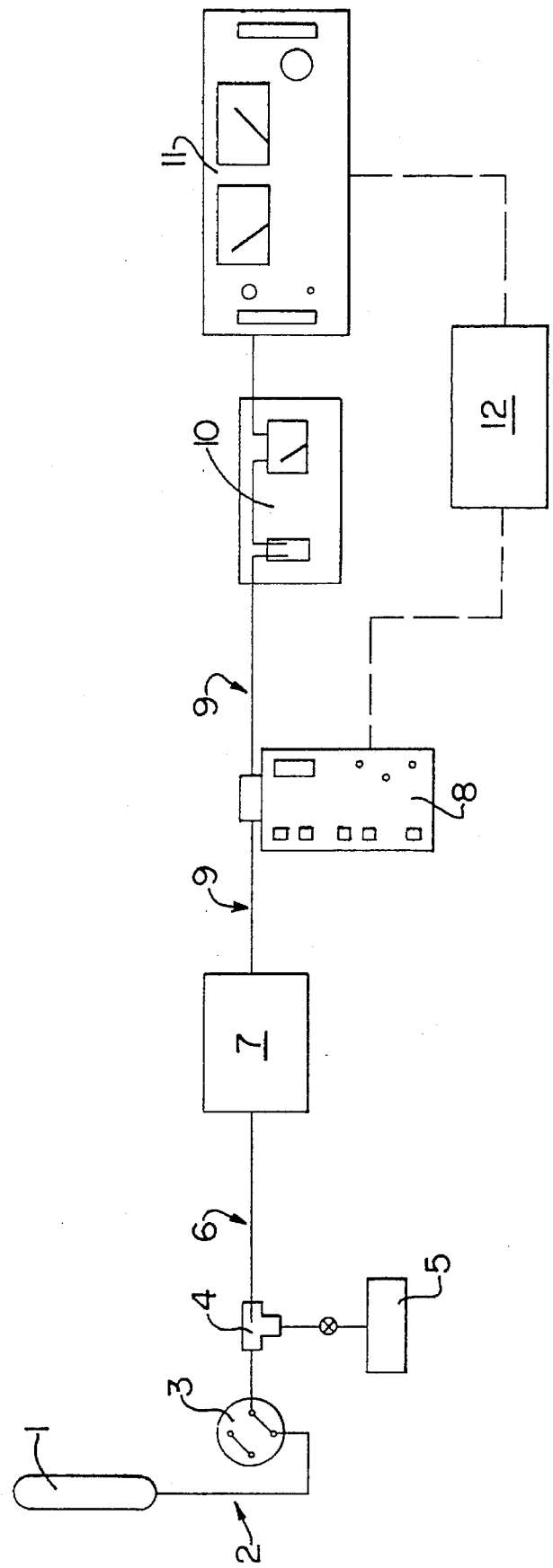
FIG. 1 provides a schematic diagram of a 2D SEC-CZE instrumentation of the present invention.

As noted above, the present invention provides a combination liquid chromatography and capillary electrophoresis separation system. In overview, the system includes a flow gating interface having an effluent channel and a gating channel formed therein, with the gating channel transversely intersecting the effluent channel at an intersection portion so that the channels are in fluid communication with one another, with the intersection portion dividing the effluent channel into an upstream portion and a downstream portion, and with the intersection portion dividing the gating channel into an upstream portion and a downstream portion. A liquid chromatography column having an outlet end is connected to the effluent channel upstream portion; and an electrophoresis capillary having an inlet end and an outlet end is included with the inlet end connected to the effluent channel downstream portion. A flush solution inlet line is connected to the gating channel upstream portion, and a flush solution outlet line is connected to the gating channel downstream portion. The intersection portion is configured so that the rate of flow of effluent from the effluent channel upstream portion to the effluent channel downstream portion decreases as the rate of flow of flush solution in the gating channel increases. Thus, by "transversely intersecting" is meant that the two channels intersect so that fluid flow in the gating channel prevents or hinders fluid flow in the effluent channel from crossing the intersection portion; rather, fluid flow in the effluent channel is directed in part or in its entirety into the gating channel downstream portion by the flush solution, with the effluent channel downstream portion simply being supplied flush solution, in whole or in part, from the gating channel. Thus, the intersection may be at a right angle or any other angle or path which achieves this desired effect. Typically, the volume of flow in the gating channel is much greater than the volume of flow in the effluent channel (i.e., at least one thousand times greater, and preferably ten thousand times greater).

While absolute dimensions are not critical to the operation of the instant invention, typically, the effluent channel upstream portion, which may be either the end terminus of the liquid chromatography column or a separate member joined to the column, has an inner diameter of from one or two microns up to 200 or 250 microns. The effluent channel downstream portion, which likewise may be the end terminus of the capillary electrophoresis capillary or a separate member joined thereto, also has an inner diameter of from one or two microns up to 200 or 250 microns. The width of the intersection portion (i.e., the distance between the end openings of the effluent channel upstream portion and effluent channel downstream portions across the transversely intersecting gating channel) is generally from 50 microns up to 200 microns, 250 microns, or even 1 millimeter.

Valve means such as a six-way valve or a combination of valves are included for regulating the flow of flush solution from the flush solution inlet line to the gating channel upstream portion. In a preferred embodiment the valve or valve system is switchable between:

(a) a first position supplying flush solution to the gating channel upstream portion; and (b) a second position supplying flush solution to the gating channel upstream portion at a lesser rate than that supplied when the valve or valve system is in the first position, with the rate of flow of effluent from the effluent channel upstream portion to the effluent channel downstream portion being greater when the valve or valve system is in the second position.

The time interval for the second position is not critical, and is typically from about one-half second to fifty seconds. The rate of sampling (i.e., the frequency at which the valve is switched to the second position) is also not critical. In general, if a two-dimensional display of data is desired, the sampling rate should be sufficient so that the effluent is sampled in the second dimension at a frequency sufficient to sample each first dimension peak at least twice in the second dimension.

In an embodiment particularly preferred for two-dimensional separation, the valve or valve system is switchable between:

(a) a first position supplying flush solution to the gating channel upstream portion at a rate sufficiently great to prevent essentially all effluent from flowing from the effluent channel upstream portion to the effluent channel downstream portion; and (b) a second position supplying flush solution to the gating channel upstream portion at a rate sufficiently small to permit essentially all effluent to flow from the effluent channel upstream portion to the effluent channel downstream portion.

As will be explained in greater detail below, the valve or valve system which comprises the valve means is preferably configured so that when the valve or valve system is in the second position the flush solution inlet line and the flush solution outlet line are connected to one another to form a closed loop, the flow of flush solution in the gating channel is essentially blocked, and essentially all effluent flows from the effluent channel upstream portion to the effluent channel downstream portion.

A power supply is typically operably connected to the capillary inlet end and the capillary outlet end in accordance with known techniques for providing a potential therebetween so that the capillary inlet end serves as an anode, the capillary outlet end serves as a cathode, and charged molecules in the capillary are carried from the capillary inlet end to the capillary outlet end by electromigration.

A detector such as a fluorescence detector is preferably operably associated with the capillary for detecting molecules in the capillary, also in accordance with known techniques. Those skilled in the art will appreciate that any suitable detector may be used, including, for example, ultraviolet absorption, mass spectrometry, electrochemical, refractive index, and chemiluminescent detectors.

For data analysis, the system may include calculating means such as a stored program running on a general purpose computer responsive to the detecting means for calculating the concentrations of molecules in the capillary, and display means such as a monochrome or color printer responsive to the calculating means for producing a two dimensional graph, one axis of the graph illustrating molecule duration in the chromatography column, and the other axis of the graph illustrating molecule duration in the capillary. Data can, of course, be provided in other form, such as a three dimensional graph (with concentration being the third axis), a chart, or a table.

A separation system will typically include a a controller, which may also be a stored program running in a general purpose computer. The controller will, in general, provide for maintaining the potential across the electrophoresis capillary sufficient to cause electromigration in the capillary when the valve means is in the first position (e.g., at 2.5 Kilovolts); and provide for maintaining the potential sufficient to cause entry of molecules from the intersection portion into the capillary when the valve means is in the second position (e.g., at 2 Kilovolts). In a preferred embodiment, the controller is programmed so that the potential is reduced (e.g., to zero Kilovolts) to a level essentially insufficient to cause entry of molecules from the intersection portion into the capillary for a first time of from 0.1 to 5 seconds (preferably one-half or one to two seconds), the first time beginning upon switching the valve means from the second position to the first position. In addition, in a preferred embodiment, the controller is also programmed so that the potential is reduced (e.g., to zero Kilovolts) to a level essentially insufficient to cause entry of molecules from the intersection portion into the capillary for a second time of from 0.1 to 5 seconds (preferably one-half or one to two seconds), the second time ending upon switching the valve means from the first position to the second position.

Numerous elements and components employed in carrying out two-dimensional separation are known in the art, as described in U.S. Pat. No. 5,131,998, the disclosure of which is to be incorporated by reference herein in its entirety, and may be employed in like manner herein, adapted as necessary to employ and carry out the features of transverse flow gating described herein.

A preferred embodiment of the present invention is discussed below with reference to the figures provided herein.

Instrumentation. The coupling of a liquid microchromatography column with capillary electrophoresis is accomplished through the use of a flow gating interface. FIG. 1 is a schematic diagram of one embodiment of the present invention. A reservoir containing sample (1) is connected by tubing (2) to a valve (3). The valve (3) is connected to a tee (4), which is connected to the SEC column (6) and a waste line (5). The SEC column (6) enters the flow gating interface (7) where the contents of SEC microcolumn (6) are transferred to CZE capillary (9), which passes through detector (8) for measurement. Power is supplied by high voltage power supply (11) and a microammeter (10) monitors current. The system is under the control of controller (12).

Chromatographic System: One embodiment of the chromatographic injection system was modified from a static split injection system which had been developed for open tubular liquid chromatography in the present inventors' laboratory. See Guthrie and Jorgenson, *J. Chromatography* 255:335 (1983). The microcolumn was removed from the static split tee and inserted into an SEC mobile phase pressure reservoir containing a small vial of sample. Head pressure of 7 bar (100 p.s.i.) was applied at the pressure reservoir for a predetermined time to inject the desired volume of sample. After the injection was complete the microcolumn was returned to the static split injection tee where the desired head pressure was applied to begin chromatography. This approach was used rather than performing a static split injection, where several hundred microliters of sample are required per injection.

In another embodiment of the present invention, a high performance liquid chromatography (HPLC) pump is used to inject sample into the microcolumn.

Electrophoresis system: Capillary electrophoresis was performed in untreated fused-silica capillaries with inner diameter of 50 µm (Polymicro Technologies, Phoenix, Ariz., U.S.A.). Capillary lengths and distance to the detection window varied and are reported in the examples. A ±30 kV high voltage power supply (Spellman High Voltage Electronics Corp., Plainview, N.Y., U.S.A.) was used in the negative high voltage mode.

Detection. One embodiment of the present invention uses ultraviolet absorbance detection means. A Linear model 200 variable wavelength UV-VIS detector outfitted with an on-column capillary flow cell was used for UV absorbance detection (Linear Instruments, Reno, Nev., U.S.A.) was used.

In another embodiment, a laser induced fluorescence (LIF) detection system utilizing a 1.5 mW green helium neon laser. See Chen et al., *J. Chromatogr.* 559, 237 (1991).

SEC-CZE Flow Gating Interface: The flow gating interface of the present invention allows an SEC microcolumn to be operationally connected to a CZE capillary. The embodiment of the flow gating device used in the present Examples consisted of two opposing plates with a gasket sandwiched between them. The inlet plate had two inlet ports, and the outlet plate two outlet ports, for the passage of flush solution and SEC effluent. The gasket separating the plates had a strip excised from it to create a channel that allowed liquid flow from the inlet ports to the outlet ports. Flush solution flow was controlled by an electrically actuated six-port valve (Valco Instruments Co., Inc., Houston, Tex., U.S.A.). A transverse flow of flush solution entered the flush solution inlet port and swept through the gasket channel to exit through the flush solution outlet port. To make an injection from the SEC microcolumn on to the CZE capillary, the flow of flush solution was temporarily shunted away from the flow gating interface and into a waste line. With the flush solution diverted, SEC effluent from the SEC port filled the gasket channel between the SEC column and the CZE capillary, and sample entered the CZE capillary. To end the injection the flush solution was again shunted to the flow gate interface, carrying all SEC effluent to waste until the next injection was made.

Figure 2:
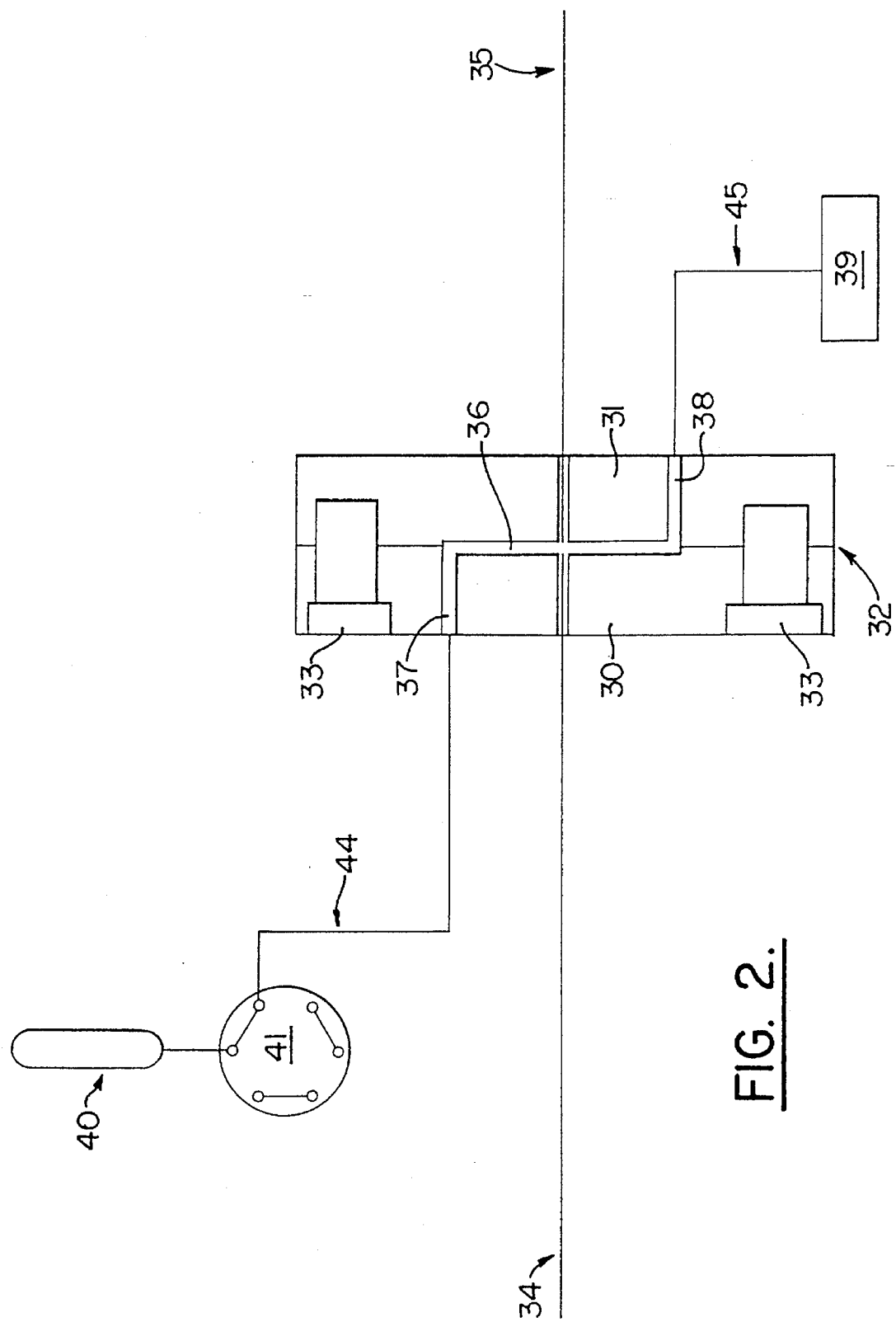
FIG. 2 is a cross-sectional view of an embodiment of the flow gating interface used in carrying out the present invention.

The embodiment of the flow gating interface used in the present Examples is diagrammed in FIG. 2. The flow gating interface described below consisted of two stainless steel plates, each ½ inch thick. The inlet plate (30) and outlet plate (31) were separated by a TEFLON™ gasket (32) of 127 µm thickness. The apparatus was assembled with 6 bolts (33) to create a liquid tight seal. The gasket had a 1 mm gating channel (36) cut in it. The outlet of the SEC microcolumn (34) was positioned directly across from the inlet of the electrophoresis capillary (35), separated only by a space of the thickness of the gasket.

The flow gating interface operated in either a "flush" mode or an "injection mode". In the flush mode, a transverse flow of flush solution from the CZE buffer reservoir (40) entered gating channel (36) through the flush solution inlet port (37) of the inlet plate (30), swept through the gating channel (36), and exited through the flush solution outlet port (38) in the outlet plate (31). This transverse flow of CZE buffer carried SEC effluent entering via the SEC microcolumn (34) away to waste (39), preventing transfer of sample from the SEC capillary (34) to the CZE capillary (35). When an injection into the CZE capillary was desired the flush solution flow was interrupted, allowing the flow of SEC effluent to carry sample into the narrow gap (the effluent channel) separating the SEC microcolumn (34) and CZE capillary (35). Electromigration from the SEC effluent flow injected sample into the CZE capillary (35). After the desired injection time the transverse flush solution flow was resumed, terminating the injection process. All SEC effluent was again carried to waste (39) until the next injection was to be made. The flow of flush solution was controlled by an electrically actuated 6 port valve (41) (Valco Instruments, Houston, Tex., U.S.A.). The flush solution inlet line (44) connecting the 6-port valve and the flow gating interface was 40 cm of PEEK tubing with an inner diameter of 0.020 inch and an outer diameter of ¹⁄₁₆ inch. The flush solution outlet line (45) was 30 cm of TEFLON™ tubing with an inner diameter of 0.040 inch ID and an outer diameter of ¹⁄₁₆ inch (Alltech Associates, Deerfield, Ill. U.S.A.). The flow of flush solution was provided by helium head pressure in one embodiment. For the 250 µm inner diameter SEC microcolumn, 3 bar (50 psi) of head pressure was applied. This pressure provided a flushing flow rate of approximately 600 uL/min. In another embodiment, the flow of flush solution was provided by an HPLC pump (Hewlett Packard HP 1050, Palo Alto, Calif. U.S.A.) and a splitter assembly, as previously-described. Oates and Jorgenson, *Analytical Chemistry*, 61, 432 (1989).

The entire interface served as the ground electrode (anode) for the CZE system. The height to the outlet of the flush solution waste line was kept level with the height of buffer in the cathodic reservoir to minimize hydrodynamic flow within the CZE capillary.

Figure 3:
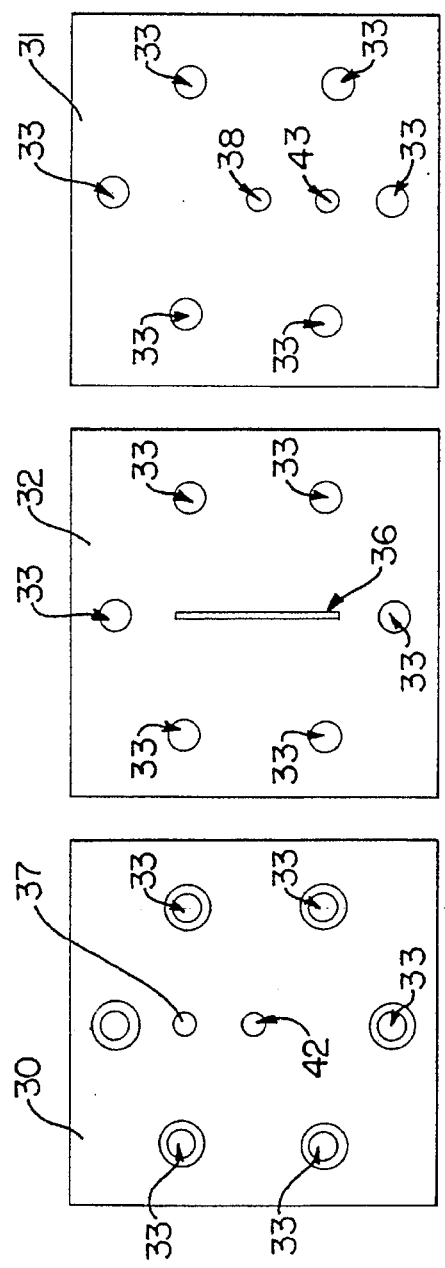
FIG. 3 is an exploded view of the inlet plate, gasket, and outlet plate, which make up the body of the flow gating interface device.

FIG. 3 is an exploded view of the plates used in the transverse flow gating device utilized in the present Examples. The mounting bolts (33) pass through the inlet plate (30), the gasket (32) and terminate in the outlet plate (31). The flush solution inlet port (37) and the SEC port (42) are located in the inlet plate (30). A 0.040 inch wide gating channel (36) has been excised from the gasket material. The flush solution outlet port (38) and the CZE port (43) are located in the outlet plate (31). Gating channel (36) is in-line with the flush solution inlet port (37), SEC port (42), CZE port (43) and flush solution outlet port (38).

Figure 4:
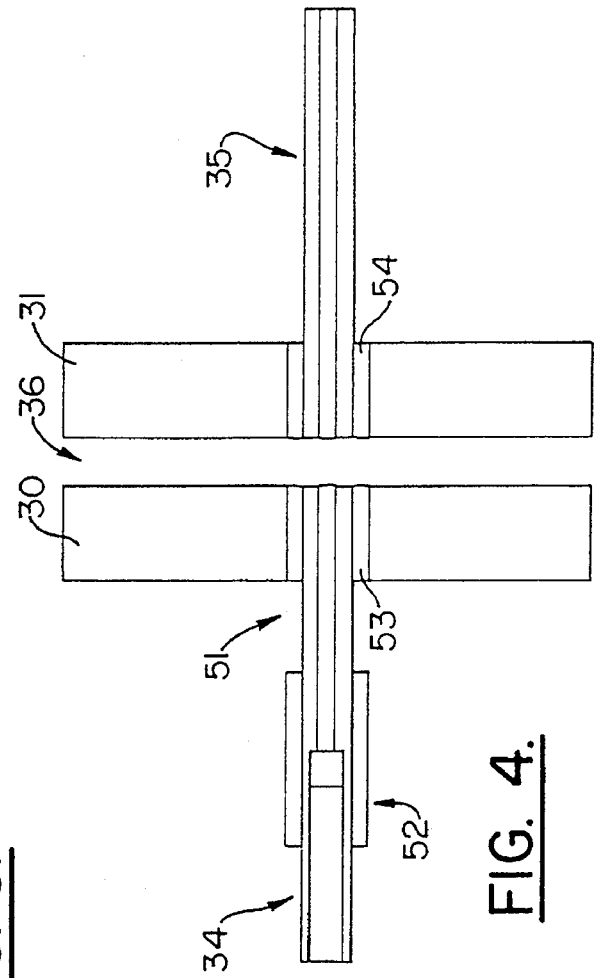
FIG. 4 is a detail view of the central region of the flow gating interface shown in FIG. 3.

FIG. 4 is a cross-sectional view of the central region of the flow gating interface. The SEC microcolumn (34) used in the examples described below was either a 250 µm inner diameter, 105 cm long column (Example 2) or a 50 µm inner diameter, 60 cm long column (Example 3). Rather than expose the relatively fragile fritted end of the SEC microcolumn to the fittings necessary to hold the capillary in place within the inlet plate (30), the microcolumn (34) was coupled to a connecting tube (51) made of fused-silica capillary. For the 250 µm inner diameter SEC microcolumn, a 3 cm long piece of 50 µm inner diameter/375 µm outer diameter fused-silica capillary was used as a connecting tube; for the 50 µm inner diameter microcolumn, 3 cm of 15 µm inner diameter/375 µm outer diameter fused-silica capillary was used. The union between the SEC microcolumn and the connecting tube was made by sleeving the two with a 1 cm piece of TEFLON™ tubing (52) with an inner diameter of 0.007 inch and an outer diameter of 1/16 inch. When heated, the TEFLON™ tubing expanded and allowed insertion of the capillaries. Upon cooling, a snug fit was obtained between the capillaries and the sleeving.

The connecting tube (51) was held in place within the inlet plate (30) using a liner (53) of TEFLON™ tubing with an inner diameter of 0.007 inch and an outer diameter of 1/16 inch, and a "Light-Touch" removable ferrule system. The connecting tubing (51) terminated flush with the inner face of the inlet plate (30) and was mounted flush with the liner (53). The CZE capillary (35) was similarly mounted within the outlet plate (31), using a liner (54) made of TEFLON™ tubing with an inner diameter of 0.007 inch and an outer diameter of 1/16 inch. Approximately 1 mm of polyimide coating was removed from the end of the CZE capillary originating at the interface to reduce analyte adsorption at the interface.

Because both the SEC connecting tube (51) and the CZE capillary (35) are mounted flush with the inner walls of the flow gating interface, they are separated by a space the thickness of the gasket. With the flow gating interface assembled as shown in FIG. 4 (connecting tube of 50 µm inner diameter, gasket of 127 µm thickness), the geometric volume of the cylinder of liquid between the SEC microcolumn and the CZE capillary is approximately 250 pL. By changing the thickness of the gasket the volume of sample "collected" in the gap between the two capillaries can be varied. This provides flexibility for using different size microcolumns operated over a range of flow rates.

Figure 5A:
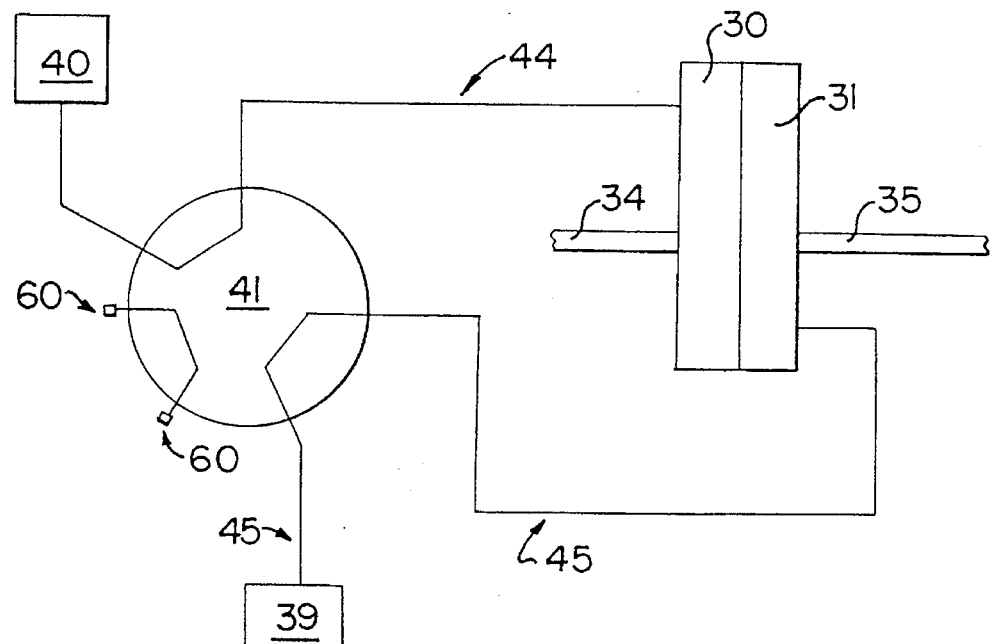
FIG. 5 shows a preferred arrangement of the the flush buffer waste line. The flush buffer outlet is connected to the six-port flush buffer valve. During the "inject" mode, the flush buffer line is configured in a closed loop (FIG. 5A). During "flush" mode, the flush buffer waste line is connected to a waste receptacle (FIG. 5B).
Figure 5B:
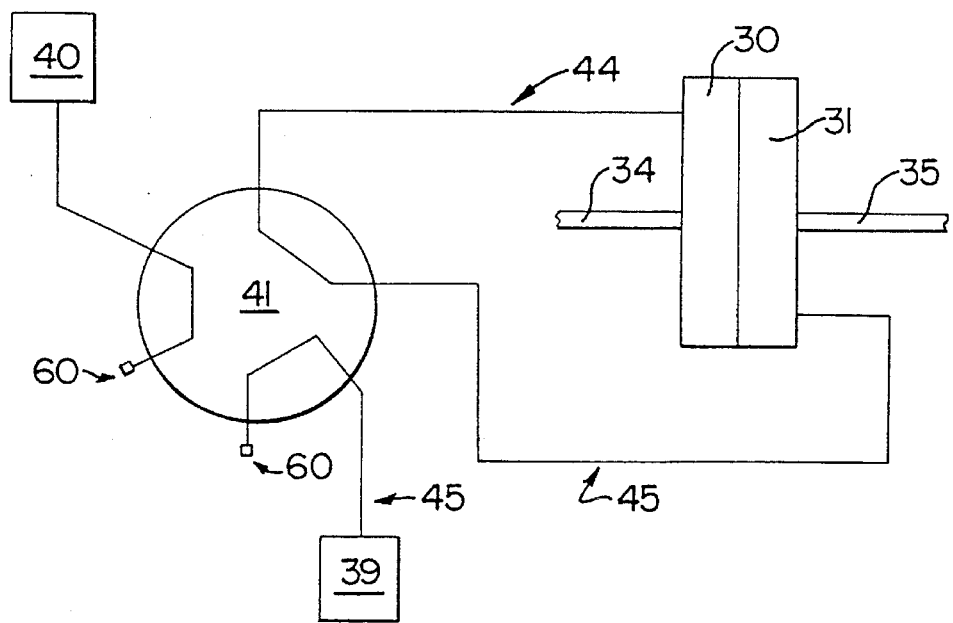

In another preferred embodiment of the apparatus, shown in FIG. 5, the flush solution waste line outlet is connected to the six-port valve in a closed loop when the apparatus is in the "inject" mode. When the apparatus was in the "flush" mode, the flush solution waste line is connected to a waste receptacle. This design prevents residual gravity flow in the gating channel during the "inject" mode. Unused ports in the six-port valve 41 are simply blocked with plugs 60.

While a preferred embodiment has been described above, those skilled in the art will appreciate that capillary electrophoresis apparatus other than capillary zone electrophoresis can be employed in practicing the present invention, including capillary gel electrophoresis, capillary isotachophoresis, micellar electrokinetic capillary chromatography, and capillary isoelectric focusing.

It will also be apparent that any type of microcolumn liquid chromatography may be used in practicing the present invention, including reverse phase chromatography columns, size exclusion chromatography columns, adsorption chromatography columns, and affinity chromatography columns. Particularly preferred are size exclusion chromatography columns.

Where appropriate, aspects of the present invention may be carried out with a first separation system other than SEC, such as by employing liquid chromatography or gel electrophoresis as the first separation system.

The present invention is useful for separating complex molecules from one another when provided in a solution containing a plurality of different molecules (i.e., a crude solution). Complex molecules which may be separated with the present invention include proteins, glycoproteins, peptides, amino acids, and polynucleic acids. The molecules may be charged molecules or may be associated with a charged group, such as in micellar electrokinetic capillary chromatography.

When fluorescence is used as the detection means the molecules to be detected may be labelled with a fluorescent group. Fluorescent molecules which may be used in connection with this invention are exemplified by fluorescein and fluorescein derivatives, dansyl chloride (5-dimethylaminonaphthylene-1-sulfonyl chloride) and analogs thereof, coumarin and coumarin analogs, and fluorescamine. Numerous other suitable fluorescent molecules are available.

The flow gating design described hereinbelow provides sample injections onto the CZE capillary that are representative of discrete points along the SEC profile. In this way, the CZE capillary analyzes "snapshots" of the SEC effluent. Sample present between injections is lost as waste. Carrying out several transfers between SEC and CZE along the width of each SEC peak ensures that the SEC column run is not "under sampled".

In one system described hereinbelow (UV detection used with CZE), further scale-down in SEC column inner diameter and flow rate is limited. The short path length for detection provided by the electrophoresis capillary, in conjunction with the inherently low sensitivity of UV detection, preclude the 2D separation of protein species present at less than approximately 0.3% (w/v). A system that employs a more sensitive detection system, such as laser induced fluorescence, would avoid this limitation.

The flow gating interface of the present invention may be manufactured by any suitable means and out of any suitable material. Such materials and means include but are not limited to the described stainless steel plates and TEFLON™ gasket assembly; thermoplastic polymers molded using conventional molding techniques such as injection molding; and thermoset polymers using conventional molding techniques such as compression molding.

The following examples are provided to illustrate the present invention, and should not be construed as limiting thereof. In these examples, 2-D means two dimensional, HPLC means High Performance Liquid Chromatography, RPLC means Reverse Phase Liquid Chromatography, °C. means degrees Centigrade, w/v means weight for volume, w/w means weight for weight, mM means milliMolar, mW means milliwatt, ml means milliliter, µL means microliter, nL means nanoliter, cm means centimeter, mm means millimeter, µm means micrometer, g means gravity, ID means inner diameter, OD means outer diameter, p.s.i. means pounds per square inch, kV means kilovolts, CZE means capillary zone electrophoresis, SEC means size exclusion chromatography, min means minutes, AUFS means absorbance units full scale, DMSO means dimethyl sulfoxide, TRITC means tetramethylrhodamineisothiocyanate, and TEA means triethylamine.

EXAMPLE 1

Preparations and Procedures

Instrument Control and Data Analysis. In Example 2, below, a Hewlett-Packard Vectra 386/25 computer (Hewlett-Packard, Palo Alto, Calif., U.S.A.) was used to control the 6-port valve, the high voltage power supply and the data collection system. The computer was equipped with a Labmaster multifunction data acquisition board (Scientific Solutions, Solon, Ohio, U.S.A.). Software written in-house with QuickBasic 4.5 (Microsoft Corp., Redmond, Wash., U.S.A.) provided control over experimental parameters and allowed for data processing and analysis. Spyglass Transform and Spyglass Format (Spyglass, Inc., Champaign, Ill., U.S.A.), imaging software for the Apple Macintosh, provided grayscale images.

In Example 3, below, a Macintosh IIcx computer equipped with a multifunction data acquisition board (National Instruments NB-MIO-16X, Austin, Tex. U.S.A.) ran under software written in house using LabView (National Instruments, Austin, Tex.). Data were presented using Spyglass software (Spyglass, Inc., Champaign, Ill., U.S.A.).

System Preparation: Prior to a 2D separation, samples are run by CZE alone in order to gauge the performance of the electrophoretic system. This ensures that any change in running time can be compensated for by adjusting CZE voltage. Testing was done by removing the SEC microcolumn from the union with the connecting tubing and replacing the SEC microcolumn with a 50 cm long, 15 µm inner diameter fused-silica capillary. The free end of this capillary was placed in a pressure reservoir containing sample. When the appropriate head pressure was applied to this reservoir, the flow rate of sample entering the interface from this capillary matched the expected flow rate of the particular SEC microcolumn being used. This provided an experimentally realistic introduction of sample into the interface. After manual injections were complete, fresh buffer was aspirated into the capillary prior to 2D operation.

Reagents. Buffer reagents were purchased from Sigma Chemical Co. (St. Louis, Mo., U.S.A.). Formamide was obtained from Fisher Scientific (Raleigh, N.C., U.S.A.). All chemicals were used as received. The buffer used for both separations was 10 mM tricine, 25 mM $Na_2So_4$, 0.005% sodium azide (w/v) adjusted to pH 8.23 with NaOH. Buffer solutions were made with deionized water purified with a Barnstead Nanopure System (Boston, Mass., U.S.A.) and were filtered with 0.2 µm nylon membrane filters from Alltech Associates (Deerfield, Ill., U.S.A.).

Microcolumn Preparation. Microcolumns used in the SEC step of the present invention were fused silica capillaries (Polymicro Technologies, Phoenix, Ariz., U.S.A.). The capillaries were slurry packed in our laboratory with Zorbax particles (Rockland Technologies Inc., Newport, Del., U.S.A.). Example 2, below, used a 250 µm inner diameter fused silica capillary of length 105 cm, packed with 6 µm, spherical, Zorbax GF450 particles. Example 3, below, used a 50 µm inner diameter fused silica capillary of length 60 cm, packed with 5 µm spherical Zorbax C8 reversed phase particles. The packing procedure has been described previously. Kennedy and Jorgenson, *J. Microcolumn Separations* 2, 120 (1990).

In preparing a SEC microcolumn from a fused silica capillary, a frit is first constructed by tapping one end of the fused silica capillary into a vial containing 100 µm diameter borosilicate glass beads (Sigma Chemical Co., St. Louis, Mo., U.S.A.). Once a band of glass beads approximately 200 µm in length has been formed in the capillary the beads are sintered by an arcing device. Optimum sintering conditions vary depending on the dimensions of the fused silica capillary, electrode spacing in the arcing device, and bead size. For best results the borosilicate beads composing the frit should not be melted; after sintering the beads should still appear as individual beads. Prior to packing the column, frits are tested by placing the inlet end in a reservoir of methanol and applying 3 bar (50 psi) of helium pressure for 30 seconds to dislodge any unstable frits. The inlet end of the microcolumn is next placed in a high pressure slurry reservoir containing a slurry of 1:10 (w/v) packing material to methanol. Methanol is forced into the reservoir at 200 bar (3,000 psi) by an Altex model 110A pump. Columns are typically packed in 8–10 hours and allowed to settle overnight under pressure. The pump is then turned off and the pressure allowed to bleed out through the column for 4 hours. The column is then rinsed with deionized water for 4 hours, followed by the running buffer which is allowed to rinse overnight.

EXAMPLE 2

Sample Transfer Using Flow Gating Interface

Figure 6:
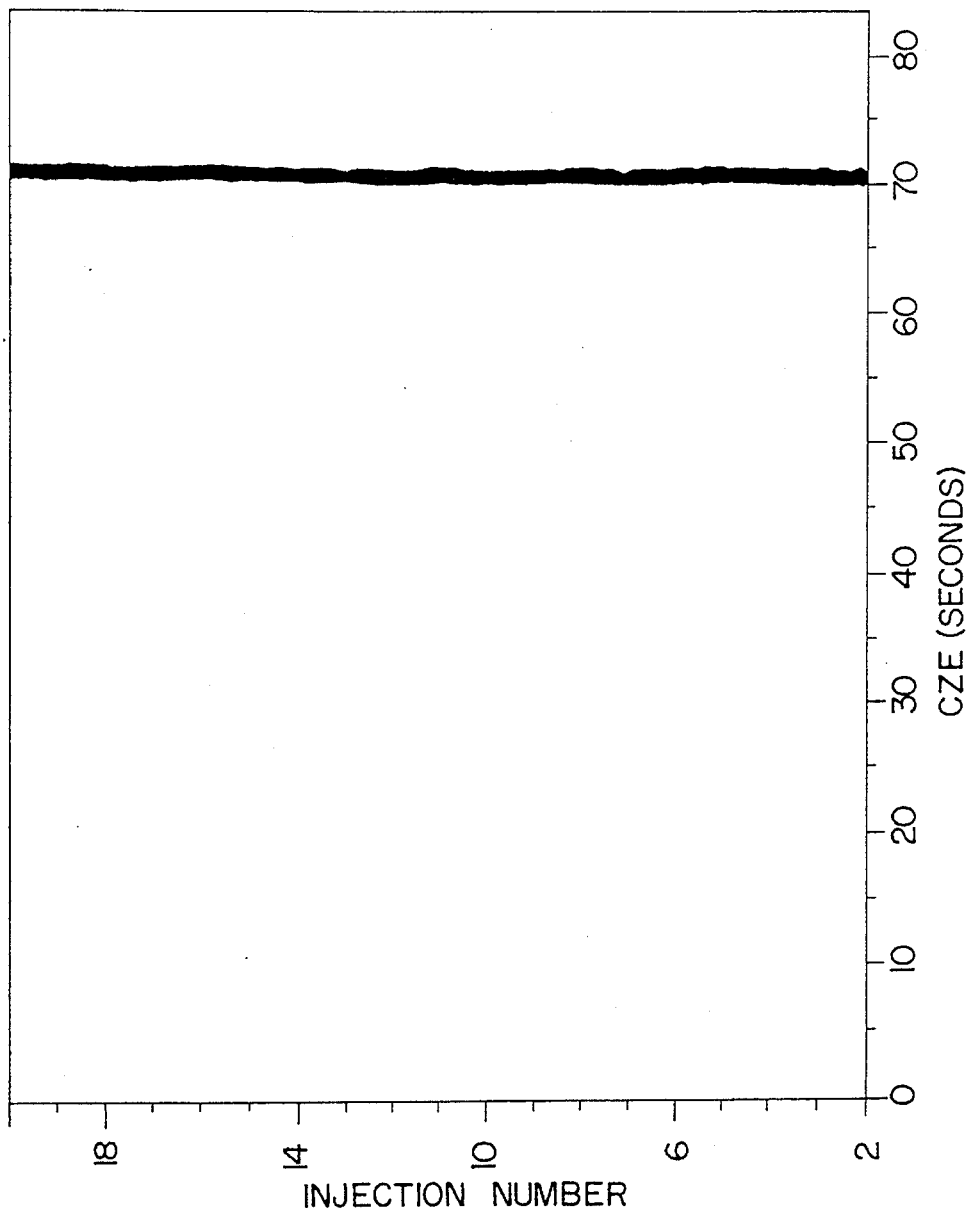
FIG. 6 shows a grayscale image of 20 repeat injections of 1% (w/v) formamide using the flow gating interface of the present invention. The formamide solution was eluted in a constant stream from a 250 μm inner diameter SEC microcolumn under 55 bar (800 p.s.i.) of head pressure. The electrophoresis capillary was 35 cm overall, 10 cm to the detection window. CZE conditions were 5 second electromigration injection at 0 kV and 2 minute runs at −7 kV. Head pressure of 3 bar (50 p.s.i.) generated a flush flow rate of 600 μL/min. The gasket thickness was 127 μm.

FIG. 6 is a grayscale image of 20 individual injections of 1% (w/v) formamide using the 2-D separation system with flow gating interface as described above. The 1% formamide solution eluted in a constant stream from the 105 cm long, 250 µm ID microcolumn under 55 bar (800 p.s.i.) of head pressure. The electrophoresis capillary was 35 cm overall, 10 cm to the detection window. CZE conditions were 5 second electromigration injection at 0 kV and 2 minute runs at −7 kV. Head pressure of 3 bar (50 p.s.i.) generated a flush flow rate of 600 µL/min. The TEFLON™ gasket thickness was 127 µm. The 5 second injection allowed sufficient flow of SEC effluent into the region between the microcolumn and the CZE capillary so that electromigration injection could occur as the high voltage slewed from 0 kV to the run voltage (−7 kV) during the switching time of the six-port valve. This injection differed from more conventional CZE electromigration in that the injection voltage was completely a function of the run voltage. In this arrangement, the amount of sample injected was controlled by the length of time that the flush flow was interrupted.

Ultraviolet absorbance detection was performed using a Linear model 200 variable wavelength UV-VIS detector outfitted with an on-column capillary flow cell (Linear Instruments, Reno, Nev., U.S.A.). Detection was done at 214 nm with a sensitivity of 0.05 absorbance units full scale (AUFS) and a rise time of 0.1 seconds.

Table 1 summarizes the reproducibility of the 20 injections in terms of percent relative standard deviation (% RSD) in migration time (first statistical moment), peak area and peak height. As shown by the well defined black band at 71 seconds in FIG. 6, very repeatable transfers of sample occurred with this interface design.

TABLE 1

| Reproducibility of 20 Injections of 1% (w/v) Formamide with the Flow Gating Interface | | | |
| --- | --- | --- | --- |
| | Migration Time | Peak Area | Peak Height |
| % RSD | 0.18% | 1.9% | 3.1% |

EXAMPLE 3

Figure 7:
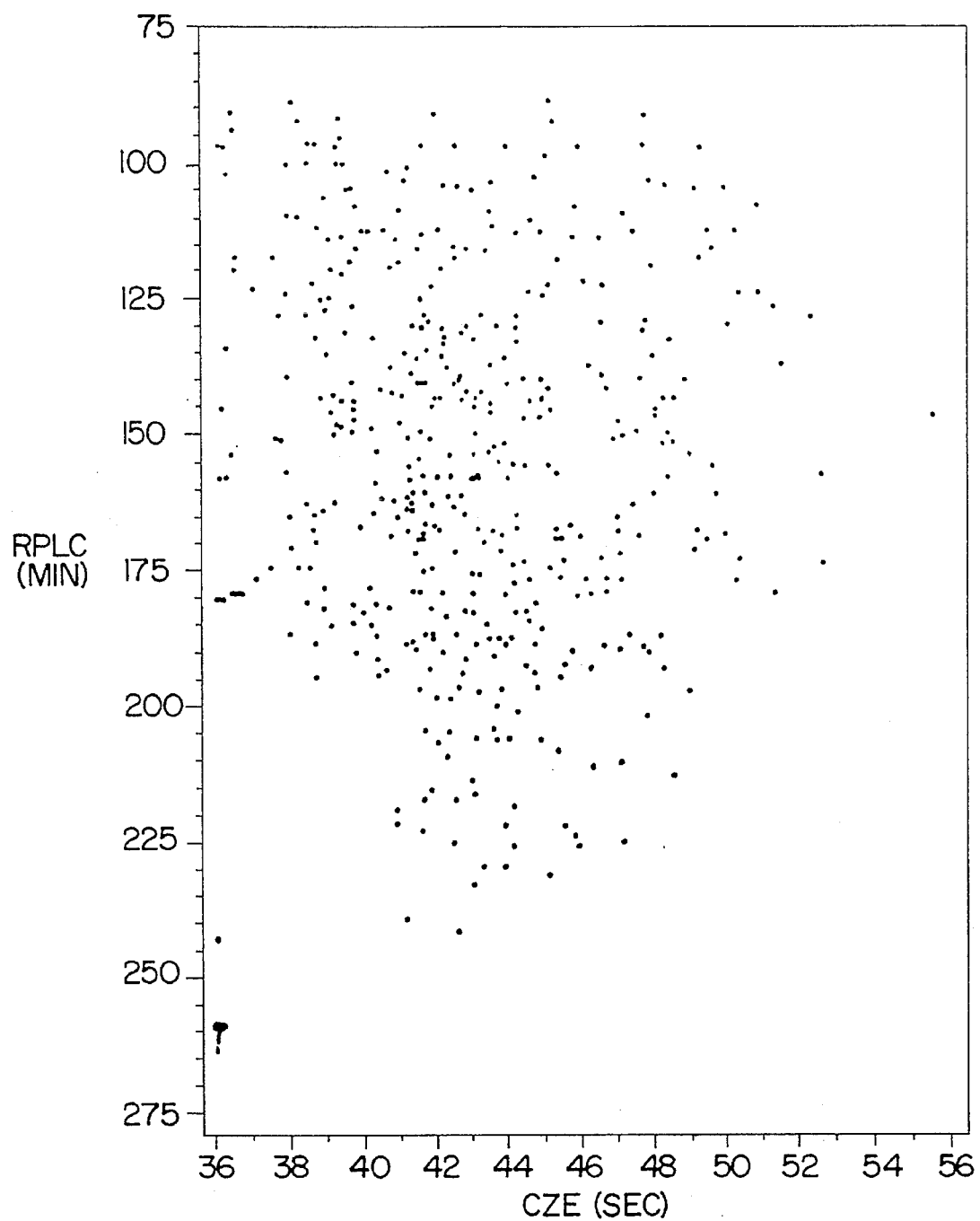
FIG. 7 shows a gray-scale image of the 2D SEC-CZE chromatoelectropherogram of the separation of tryptic digest of reduced porcine thyroglobulin using the flow gating interface of the present invention. Chromatographic conditions were: 60 cm long, 50 μm inner diameter SEC microcolumn; 5 μm particle size Zorbax C8 reversed phase packing material; and elution gradient of 15–45% acetonitrile over 240 minutes. Capillary electrophoresis conditions were: 15 μm inner diameter, 25 cm long capillary, with 15.5 cm to detection window; injection conditions of −1 kV for 3 seconds; and run conditions of −22.5 kV for 58 seconds. Laser induced fluorescence was used to detect the tetramethylrhodamineisothiocyanate (TRITC) labeled tryptic fragments of thyroglobulin.

2D Separation Using Flow Gating Interface: Tryptic Digest of Reduced Porcine Thyroglobulin FIG. 7 shows a gray-scale image of the 2D SEC-CZE chromatoelectropherogram of the separation of a tryptic digest of reduced porcine thyroglobulin using the flow gating interface of the present invention. The tryptic fragments of reduced porcine thyroglobulin were labeled with TRITC; laser induced fluorescence was used to detect the TRITC labeled fragments.

Porcine thyroglobulin was digested with trypsin (30/1 w/w) for 24 hours at 37° C. in 0.1M boric acid, pH=8.4. After enzymatic digest, the sample was 0.2 µm filtered (Gelman; Baxter Scientific, McGaw Park, Ill. U.S.A.). The fluorescent derivitizing reagent TRITC was dissolved in DMSO at 10 mg/ml. A 25 µL aliquot of TRITC solution was combined with 75 µL of digested thyroglobulin (2 mg/ml). The reaction was allowed to proceed at room temperature for 4 hours in the dark. For all tagging reactions, the tryptic peptides were in 3-fold molar excess to TRITC which had a final concentration of 5.6 mM in the reaction mixture. This reaction mixture was diluted 100-fold into the initial SEC mobile phase prior to injection.

A 60 cm, 50 µm inner diameter SEC microcolumn was used, packed with 5 µm particle size Zorbax C8 reversed phase packing material. An elution gradient of 15–45% acetonitrile over 240 minutes was used. The electrophoresis capillary was 25 cm long and had an inner diameter of 15 µm; it was 15.5 cm to the detection window. Electromagnetic injection conditions were −1 kV for 3 seconds; run conditions were −22.5 kV for 58 seconds. A flushing flow rate of 400 µL/min was generated using a high performance liquid chromatography (HPLC) pump (Hewlett-Packard 1050 pump, Hewlett-Packard, Palo Alto, Calif. U.S.A.) and a splitter assembly, as previously described. Oates and Jorgenson, *Analytical Chemistry*, 61, 432 (1989). The CZE run buffer in the negative high voltage reservoir and in the flush pump was 10 mM $Na_2HPO_4$ plus 20 mM TEA, pH=11.0.

A high sensitivity laser induced fluorescence detection system utilizing a 1.5 mW green helium neon laser was used. Detection was performed at 543.5 nm. Fluorescence was detected at 90° from excitation with a photomultiplier tube. Data collection and timing of the six-port valve and high voltage power supply were under computer control. A Macintosh IIcx equipped with a multifunction data acquisition board (National Instruments NB-MIO-16X, Austin, Tex. U.S.A.) ran under software written in house using LabView (National Instruments, Austin, Tex.). Data were presented using Spyglass software.

As shown by the distinct points of FIG. 7, very fine resolution can be achieved with this interface design.

The foregoing is illustrative of the present invention, and not to be construed as limiting thereof. The invention is defined by the following claims, with equivalents of the claims to be included therein.

That which is claimed is:

1. A flow gating interface having an effluent channel and a gating channel formed therein, said gating channel transversely intersecting said effluent channel at an intersection portion so that said channels are in fluid communication with one another, with said intersection portion dividing said effluent channel into an upstream portion and a downstream portion, and with said intersection portion dividing said gating channel into an upstream portion and a downstream portion, wherein said gating channel has a larger cross-sectional area than said effluent channel, and wherein said flow gating interface further comprises, valve means operably connected to said gating channel upstream portion for regulating a flow of flush solution to said gating channel upstream portion.

2. A flow gating interface according to claim 1, wherein said valve means is switchable between:

a first position supplying flush solution to said gating channel upstream portion; and a second position supplying flush solution to said gating channel upstream portion at a lesser rate than that supplied when said valve means is in said first position, and with the rate of flow of effluent from said effluent channel upstream portion to said effluent channel downstream portion being greater when said valve means is in said second position.

3. A flow gating interface according to claim 2, configured so that when said valve means is in said second position said flush solution inlet line and said flush solution outlet line are connected to one another to form a closed loop, the flow of flush solution therein is essentially blocked, and essentially all effluent flows from said effluent channel upstream portion to said effluent channel downstream portion.

4. A flow gating interface according to claim 1, wherein said valve means is switchable between:

a first position supplying flush solution to said gating channel upstream portion at a rate sufficiently great to prevent essentially all effluent from flowing from said effluent channel upstream portion to said effluent channel downstream portion; and a second position supplying flush solution to said gating channel upstream portion at a rate sufficiently small to permit essentially all effluent to flow from said effluent channel upstream portion to said effluent channel downstream portion.

5. A flow gating interface according to claim 1, wherein said effluent channel downstream portion has an inner diameter of from one micron to 250 microns.

6. A flow gating interface according to claim 1, wherein said intersection portion is from 50 to 250 microns in width.

7. A flow gating interface system, comprising:

a flow gating interface having an effluent channel and a gating channel formed therein, said gating channel having a cross sectional area larger than said effluent channel cross sectional area, said gating channel transversely intersecting said effluent channel at an intersection portion so that said channels are in fluid communication with one another, with said intersection portion dividing said effluent channel into an upstream portion and a downstream portion, and with said intersection portion dividing said gating channel into an upstream portion and a downstream portion; and valve means operably connected to said gating channel upstream portion for regulating a flow of flush solution to said gating channel upstream portion;

wherein said valve means is switchable between a first position supplying flush solution to said gating channel upstream portion at a first rate sufficiently great to prevent essentially all effluent in said effluent channel upstream portion from flowing to said effluent channel downstream portion, and a second position supplying flush solution to said gating channel upstream portion at a second rate lesser than said first rate and sufficiently small to permit essentially all effluent in said effluent channel upstream portion to flow to said effluent channel downstream portion.

8. A flow gating interface system according to claim 7, wherein said interface system includes a liquid chromatography column having an outlet end connected to said effluent channel upstream portion, and further including an electrophoresis capillary having an inlet end and an outlet end, said inlet end connected to said effluent channel downstream portion.

9. A flow gating interface system according to claim 8, further comprising power supply means operably connected to said capillary inlet end and said capillary outlet end for providing a potential therebetween so that said capillary inlet end serves as an anode, said capillary outlet end serves as a cathode, and charged molecules in said capillary are carried from said capillary inlet end to said capillary outlet end by electromigration.

10. A flow gating interface system according to claim 9, further comprising a controller, said controller including:

means for maintaining said potential sufficient to cause electromigration in said capillary when said valve means is in said first position; and means for maintaining said potential sufficient to cause entry of molecules from said intersection portion into said capillary when said valve means is in said second position.

11. A flow gating interface system according to claim 10, said controller further comprising means for reducing said potential to a level essentially insufficient to cause entry of molecules from said intersection portion into said capillary for a time of from 0.1 to 5 seconds, said time beginning upon switching said valve means from said second position to said first position.

12. A flow gating interface system according to claim 11, wherein said time is from one to two seconds.

13. A flow gating interface system according to claim 10, said controller further comprising means for reducing said potential to a level essentially insufficient to cause entry of molecules from said intersection portion into said capillary for a time of from 0.1 to 5 seconds, said time ending upon switching said valve means from said first position to said second position.

14. A flow gating interface system according to claim 13, wherein said time is from one to two seconds.

15. A flow gating interface system according to claim 8, further comprising a detector operably associated with said capillary for detecting molecules in said capillary.

16. A flow gating interface system according to claim 7, wherein said effluent channel upstream portion has an inner diameter of from one micron to 250 microns.

17. A flow gating interface system according to claim 7, wherein said effluent channel downstream portion has an inner diameter of from one micron to 250 microns.

18. A flow gating interface system according to claim 7, wherein said intersection portion is from 50 to 250 microns in width.

19. A method of gating fluid flow, comprising:

providing a first fluid stream;

providing a second fluid stream of larger cross sectional area than said first fluid stream, said first and second fluid streams transversely intersecting to divide said first fluid stream into an upstream portion and a downstream portion, and to divide said second fluid stream into an upstream portion and a downstream portion; and alternately supplying fluid to said second fluid stream upstream portion at (i) a first rate sufficiently great to divert essentially all of said first fluid stream to said second fluid stream downstream portion, and (ii) at a second rate lesser than said first rate and sufficiently small to permit essentially all fluid in said first fluid stream upstream portion to flow to said first fluid stream downstream portion.

20. A method according to claim 19 wherein said first fluid stream is contained within a microcolumn.

21. A method according to claim 19 wherein said first fluid stream is contained within a microcolumn and said second fluid stream is contained within a column having a cross sectional area at least 60× greater than that of said microcolumn.

22. A method according to claim 19 wherein said alternately supplying step is carried out by providing a valve switchable between a first position providing fluid at said first rate, and a second position providing fluid at said second rate.

* * * * *